US008914925B2

(12) United States Patent
Angott

(10) Patent No.: US 8,914,925 B2
(45) Date of Patent: Dec. 23, 2014

(54) MOBILE DIAGNOSTIC ASSEMBLY

(75) Inventor: Paul G. Angott, Bloomfield Hills, MI (US)

(73) Assignee: Wayne County Employees' Retirement System, Detroit, MI (US)

(*) Notice: Subject to any disclaimer, the term of this patent is extended or adjusted under 35 U.S.C. 154(b) by 384 days.

(21) Appl. No.: 13/368,627

(22) Filed: Feb. 8, 2012

(65) Prior Publication Data

US 2013/0198960 A1    Aug. 8, 2013

(51) Int. Cl.
*A61G 13/12* (2006.01)

(52) U.S. Cl.
USPC ............ 5/621; 5/613; 5/622; 5/731; 5/735; 5/661; 5/725; 128/845

(58) Field of Classification Search
USPC ............ 5/600, 601, 613, 621, 622, 630, 631, 5/730, 731, 735, 503.1, 658, 661, 725; 128/845, 846
See application file for complete search history.

(56) References Cited

U.S. PATENT DOCUMENTS

| | | | |
|---|---|---|---|
| 3,973,126 A * | 8/1976 | Redington et al. | 378/17 |
| 4,015,836 A * | 4/1977 | Redington et al. | 5/601 |
| 4,298,009 A * | 11/1981 | Mezrich et al. | 600/443 |
| 4,341,222 A * | 7/1982 | Gardineer et al. | 600/437 |
| 5,078,142 A * | 1/1992 | Siczek et al. | 600/407 |
| 5,415,169 A * | 5/1995 | Siczek et al. | 600/427 |
| 5,564,438 A * | 10/1996 | Merchant | 5/613 |
| 5,569,266 A | 10/1996 | Siczek | |
| 5,609,152 A * | 3/1997 | Pellegrino et al. | 600/429 |
| 6,199,233 B1 | 3/2001 | Kantrowitz et al. | |
| 6,298,114 B1 * | 10/2001 | Yoda | 378/37 |
| 6,560,310 B2 * | 5/2003 | Stark | 378/37 |
| 6,662,042 B1 * | 12/2003 | Grable | 600/473 |
| 7,458,118 B2 | 12/2008 | Bak | |
| 7,694,370 B1 * | 4/2010 | Lee | 5/632 |
| 7,763,864 B2 * | 7/2010 | Formenti | 250/453.11 |
| 7,771,360 B2 * | 8/2010 | Johnson et al. | 600/459 |
| 8,366,617 B2 * | 2/2013 | Johnson et al. | 600/437 |
| 8,475,377 B2 * | 7/2013 | Angott | 600/437 |

(Continued)

FOREIGN PATENT DOCUMENTS

WO          9855013           12/1998
WO       2004041089 A2         5/2004

OTHER PUBLICATIONS

International Search Report dated Apr. 16, 2013.

*Primary Examiner* — Nicholas Polito
*Assistant Examiner* — David R Hare
(74) *Attorney, Agent, or Firm* — Dickinson Wright PLLC

(57) ABSTRACT

A mobile diagnostic assembly (20) of the type for supporting a patient in a prone position along an examination surface includes a support frame (22) having a top (26) extending between a front edge (38) and a rear edge (40) and defining at least one opening (48) for receiving pendant breasts of the patient in the prone position. The support frame (22) is movable to a testing position for disposing the rear edge (40) adjacent the examination surface. A flap (50) extends from the rear edge of the top for overlaying an examination surface in the testing position to support the prone patient along the examination surface and said flap and said top to prevent movement of the support frame relative to the examination surface. A pivot (54) is disposed between the flap and the top for establishing rotation of the flap from the testing position to cover said top.

1 Claim, 4 Drawing Sheets

(56) References Cited

U.S. PATENT DOCUMENTS

| | | |
|---|---|---|
| 2004/0097811 A1* | 5/2004 | Smith et al. .................. 600/448 |
| 2005/0143638 A1 | 6/2005 | Johnson et al. |
| 2006/0009693 A1* | 1/2006 | Hanover et al. .............. 600/407 |
| 2008/0043905 A1* | 2/2008 | Hassanpourgol .............. 378/37 |
| 2008/0077005 A1* | 3/2008 | Piron et al. ................... 600/411 |
| 2008/0201850 A1* | 8/2008 | Brito et al. ....................... 5/601 |
| 2009/0080604 A1* | 3/2009 | Shores et al. .................. 378/37 |
| 2009/0143674 A1* | 6/2009 | Nields et al. ................. 600/437 |
| 2011/0047702 A1 | 3/2011 | Diao |
| 2011/0091018 A1 | 4/2011 | Tybinkowski et al. |
| 2013/0019876 A1* | 1/2013 | Zacharopoulos et al. .... 128/845 |

* cited by examiner

MOBILE DIAGNOSTIC ASSEMBLY

BACKGROUND OF THE INVENTION

1. Field of the Invention

A mobile diagnostic assembly including a diagnostic unit and of the type for supporting a patient in a prone position along an examination surface.

2. Description of the Prior Art

The mobile diagnostic assemblies to which the subject invention pertains are assemblies which are movable to a testing position for disposing the assembly adjacent an examination surface. One such assembly is illustrated in U.S. Patent Application 2008/0077005 to Piron wherein the assembly includes a support frame having a top extending between a front edge and a rear edge and the assembly is movable to a testing position for disposing the rear edge adjacent the examination surface. In addition, the top defines at least one opening for receiving pendant breasts of the patient in the prone position.

Although the prior art diagnostic assemblies can include a mechanical attachment such as a clamp, straps or the like to prevent relative movement of the support frame in the testing position, such an assembly requires a nurse, technician or the like to establish a mechanical connection with the examination table. Correspondingly, when the support frame is disposed in the testing position, this mechanical attachment is often located in a place or area with limited access, thus making it difficult for the nurse or technician to establish the mechanical connection. Also, use of a mechanical attachment requires the diagnostic assemblies to be individually tailored to each targeted end use. In other words, the effectiveness of mechanical attachments are dependent on each individual examination surface, and thus add logistics and manufacturing costs to the diagnostic assembly. Accordingly, there remains a need for a design which can accommodate a variety of examination surfaces while correspondingly reducing manufacturing costs and set-up time when performing the diagnostic test.

SUMMARY OF THE INVENTION

The invention provides for a flap extending from the rear edge of the top for overlaying the examination surface in the testing position and supporting the prone patient along the examination surface and the flap and the top to prevent movement of the support frame relative to the examination surface.

Advantages of the Invention

The flap is advantageous because the prone patient supported on the flap prevents relative movement of the support frame. In other words, weight of the prone patient acting upon the flap eliminates the need to use a mechanical attachment with the diagnostic assembly. Accordingly, the flap provides a simple, quick and effective way to prevent movement of the support frame that ultimately reduces set-up time, and thus costs, for performing a diagnostic test using the mobile diagnostic assembly. In addition, since a mechanical attachment is not required, the flexibility of the mobile diagnostic assembly is increased because the flap can overlay a variety of examination surfaces. Correspondingly, the flap reduces manufacturing costs since mechanical components tailored for each end user do not need to be incorporated into individual mobile diagnostic assemblies.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE ENABLING EMBODIMENTS

Figure 1:
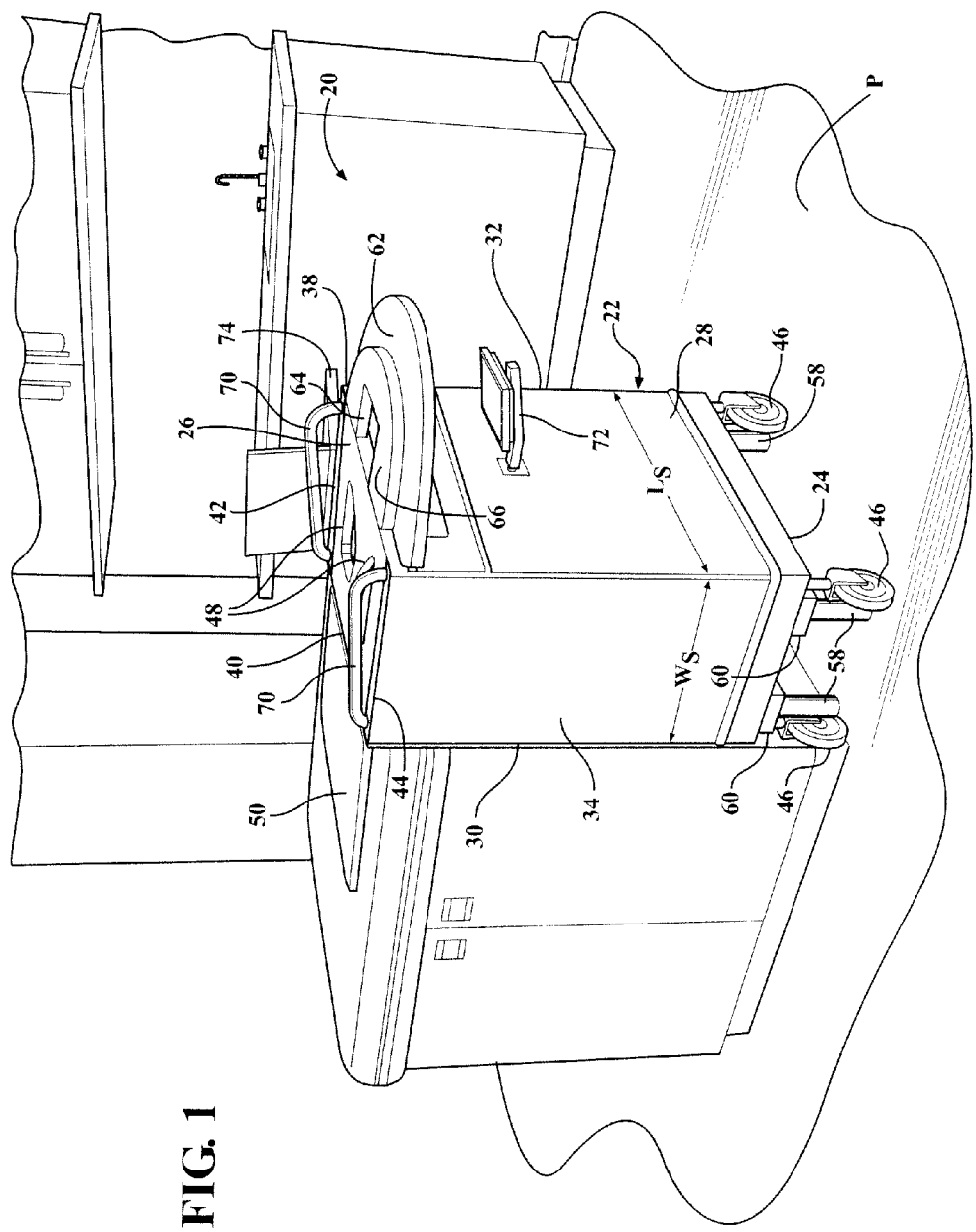
FIG. 1 is a perspective view of a mobile diagnostic assembly showing a support structure disposed in a testing position and a flap extending from the support structure and overlaying an examination surface.
Figure 2:
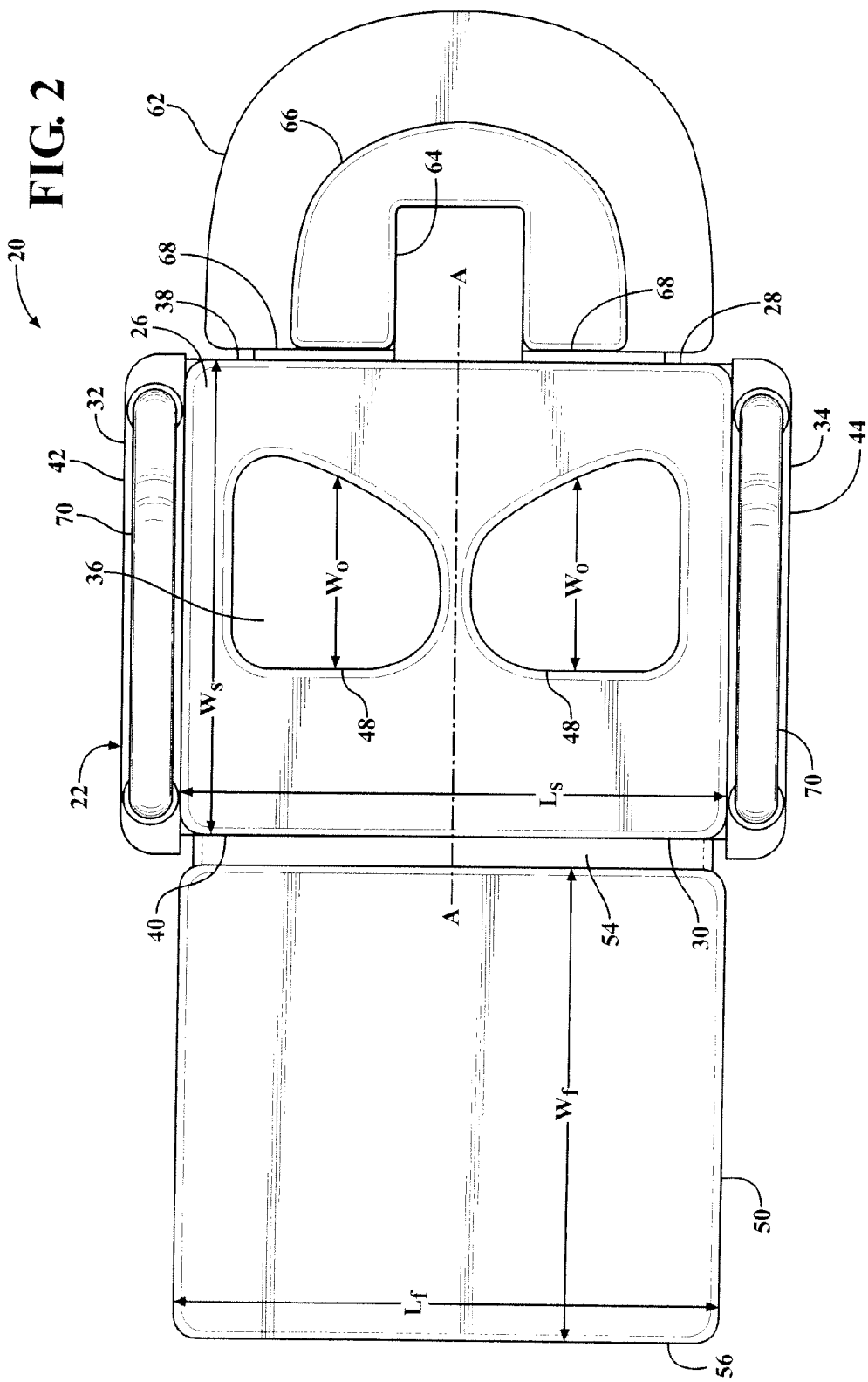
FIG. 2 is a top view of the mobile diagnostic assembly showing a top extending between a front edge and a rear edge and defining a plurality of openings disposed in spaced and aligned relationship relative to a surface axis and a pivot interconnecting the flap and the top.
Figure 3:
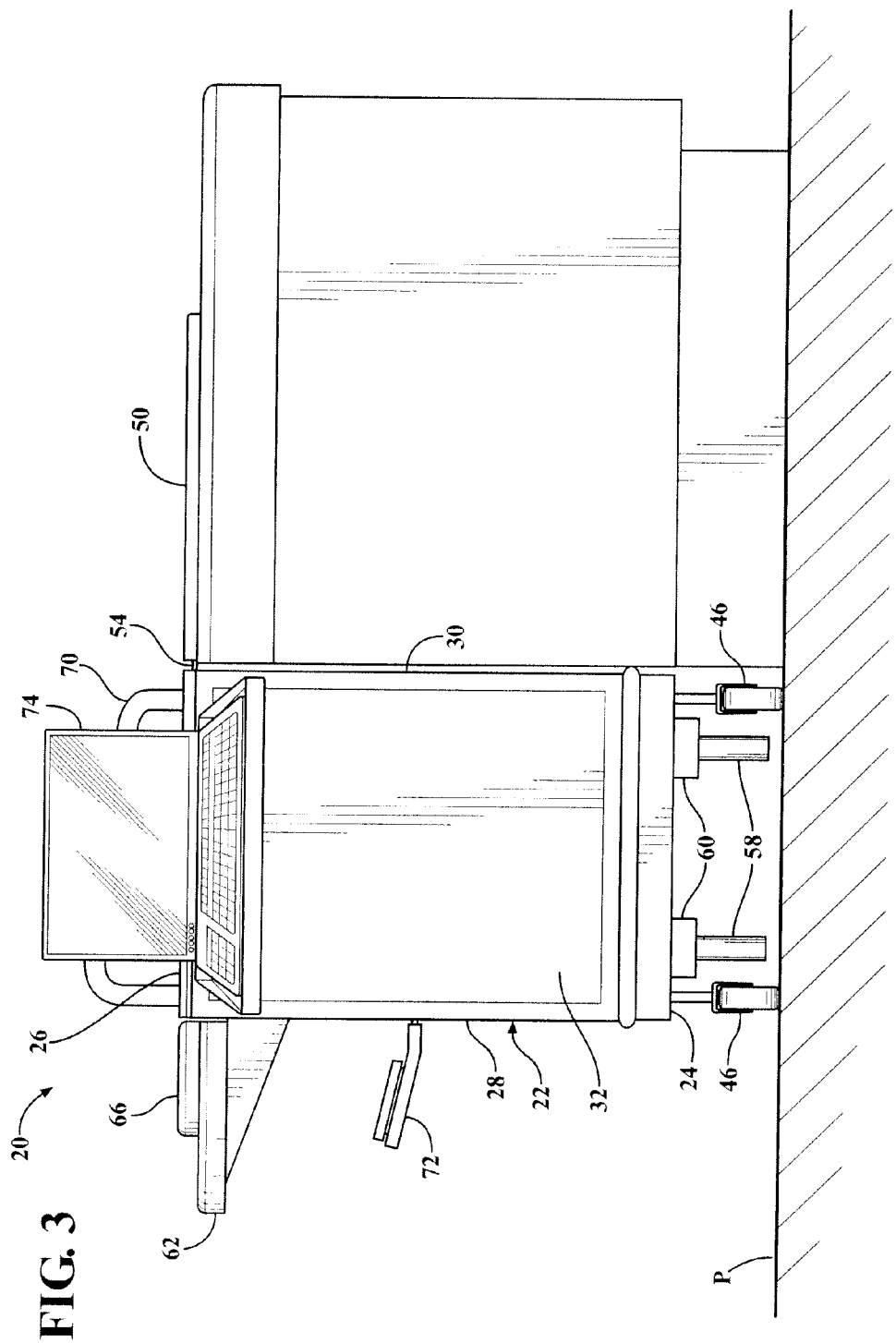
FIG. 3 is a side view of the mobile diagnostic assembly.
Figure 4:
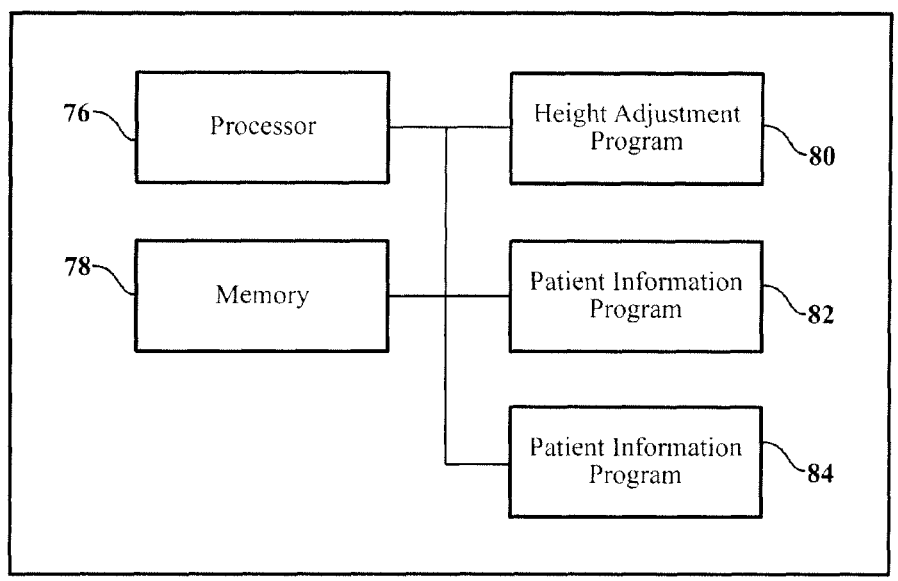
FIG. 4 is a schematic diagram of a computer showing a processor and a memory and a plurality of computer programs.

Referring to the Figures, wherein like numerals indicate corresponding parts throughout the several views, a mobile diagnostic assembly 20 including a diagnostic unit is generally shown in FIGS. 1-3. The mobile diagnostic assembly 20 is of the type for supporting a patient in a prone position along an examination surface.

The assembly 20 includes a support frame 22 having four sides extending between a bottom 24 and a top 26 to define a front side 28 and a rear side 30 and a left side 32 and a right side 34. The assembly 20 also includes an interior 36 disposed between the top 26 and bottom 24 and inwardly from the sides 28, 30, 32, 34 for housing the diagnostic unit. The top 26 extends between a front edge 38 and a rear edge 40 to define a left edge 42 and a right edge 44, and a plurality of caster wheels 46 are attached to the bottom 24 and extend to a rolling plane P for establishing rolling movement of the assembly 20 over a support. Accordingly, the mobile diagnostic assembly 20 can be moved within an examination room or between adjacent examination rooms to and from a testing position for disposing the rear edge 40 adjacent the examination surface. The top 26 also defines at least one opening 48 for receiving pendant breasts of the patient in the prone position to allow the diagnostic unit to perform a diagnostic test on the pendant breasts. As best shown in FIG. 1, a flap 50 extends from the rear edge 40 of the top 26 for overlaying the examination surface in the testing position and supporting the prone patient along the examination surface and the flap 50 and the top 26 to prevent movement of the support frame 22 relative to the examination surface. In other words, when the patient is disposed in the prone position, the flap 50 receives weight of the prone patient to establish a frictional force between the flap 50 and the examination surface to prevent movement of the mobile diagnostic assembly 20. This is advantageous because since the flap 50 is part of the mobile diagnostic assembly 20, the flap 50 acts as a safety feature by preventing movement of the assembly 20 which could potentially injure the patient. In other words, when a patient gets on the examination surface, there is a tendency for the patient to slide or move the assembly 20 away from the examination surface. This would be a dangerous situation because the patient could fall off the examination surface. Accordingly, the flap 50 helps to keep the assembly 20 from sliding or moving away while the patient is getting onto the examination surface to avoid this situation. In addition, by reducing movement of the mobile assembly 20, the flap 50 helps to stabilize the diagnostic unit during testing, and thus improves the results from the diagnostic test performed on the pendant breasts. In addition, the flap 50 eliminates the need to use a mechanical attachment such as a clamp, straps or the like to prevent relative movement between the support frame 22 and the examination surface. Accordingly, the flap 50 helps to reduce set-up time of the mobile diagnostic assembly 20 in the testing position.

In the preferred embodiment, as best shown in FIG. 2, the at least one opening 48 includes a pair of openings 48 disposed in spaced and aligned relationship relative to a surface axis A which extends along the top 26 in parallel and equidistant relationship to the left and right edges 42, 44. In addition, the top 26 includes a chest support 52 extending between the openings 48 and aligned on the surface axis A. In the preferred embodiment the top 26 is radially deformable relative to the surface axis A to establish a concave shape for conforming the top 26 to a shape of the prone patient. In addition, the openings 48 define an opening width $W_o$ increasing from the surface axis A toward the left and right sides 32, 34 for providing access to lymph nodes of the prone patient.

As also best shown in FIG. 2, a pivot 54 interconnects the flap 50 and the top 26 for establishing rotation of the flap 50 in either a horizontal or vertical direction from the testing position to cover the top 26 and the openings 48. This is advantageous because the flap 50 essentially acts as a lid to prevent anything from entering the interior 36 of the support frame 22 which could damage the diagnostic unit or require cleaning of the interior 36 of the assembly 20. In addition, when the flap 50 covers the top 26, the flap 50 provides a flat surface to hold items when not in use. This is especially convenient when space is limited in the examination room or when the assembly 20 is moved between adjacent examination rooms. Since there may be items that need to travel with the assembly 20, the flap 50 adds this convenience to the mobile diagnostic assembly 20. In addition, the flap 50 can be rotated to dispose the flap 50 in parallel and abutting relationship along the rear side 30 of the support frame 22 for providing access to the interior 36 and the diagnostic unit as may be required. In addition, when the flap 50 is disposed in parallel and abutting relationship along the rear side 30, the patient could also lean over the assembly 20 to allow performance of the diagnostic test without the need for the examination surface. In an alternative embodiment, the pivot 54 could be replaced with a slide, and the slide would allow the flap 50 to extend from the top 26 for overlaying the examination surface.

In the preferred embodiment of the assembly 20, the front and rear sides 28, 30 have a support length $L_s$ that is less than or equal to thirty six inches and the left and right sides 32, 34 have a support width $W_s$ that is less than or equal to twenty four inches. Correspondingly, as best shown in FIG. 2, the flap 50 extends from the pivot 54 to a flap end 56 to define a flap width $W_f$ that is less than or equal to the support width $W_s$ for disposing the flap 50 between the left and right edges 42, 44. In addition, the flap 50 has a flap length $L_f$ that is less than or equal to the support length $L_s$ for preventing the flap 50 from extending beyond the front edge 38. In the preferred embodiment, the flap width $W_f$ is twenty-four inches and the flap length $L_f$ is thirty-six inches. The size of the mobile diagnostic assembly 20 is advantageous because it allows for the assembly 20 to be easily moved between examination rooms when the assembly 20 is used in doctor's offices. In other words, since approved doorways in doctor offices are thirty-six inches wide, the support length $L_s$ and support width $W_s$ of the mobile diagnostic assembly 20 allows the assembly 20 to be removed from one examination room and subsequently placed in an adjacent examination room. This is advantageous because it allows the mobile diagnostic assembly 20 to be shared within a doctor's office and does not require a diagnostic assembly 20 dedicated to each individual examination room, thus reducing capital investment for the end use of the mobile diagnostic assembly 20. In addition, since the mobile diagnostic assembly 20 is small, portable and lightweight, the assembly 20 can easily be moved by one person.

As best shown in FIG. 1, a plurality of legs 58 extend downwardly from the bottom 24 and are disposed in spaced relationship to the rolling plane P for allowing rolling movement of the assembly 20. A mechanical height adjuster 60 interconnects each of the legs 58 with the frame for elongating the legs 58 past the rolling plane P to raise the caster wheels 46 from the rolling plane P and raise the support frame 22 to align the top 26 with the examination surface. This is advantageous because it allows the mobile diagnostic assembly 20 to accommodate any height of the examination surface. In addition, the interaction of the legs 58 with the rolling plane P also assists in preventing movement of the support frame 22 relative to the examination surface. Also, in the preferred embodiment, the mechanical height adjuster 60 includes electric motors, however any comparable mechanism could be used to elongate the legs 58.

As best shown in FIG. 1, a head rest 62 extends from the front edge 38 of the top 26 for supporting a head of the prone patient. The head rest 62 defines a face opening 64 aligned on the surface axis A for accommodating a face of the prone patient and a face cushion 66 is disposed circumferentially about the face opening 64 and extends upwardly from the head rest 62. As best shown in FIG. 2, a support hinge 68 interconnects the head rest 62 and the support frame 22 for allowing the head rest 62 to rotate relative to the support hinge 68 and establish parallel and abutting relationship with the front side 28 of the support frame 22. As best shown in FIG. 1, a plurality of handles 70 extend upwardly from the top 26 and are disposed next adjacent the left and right edges 42, 44 for assisting the patient in the prone position. The handles 70 are advantageous because they allow for easy access when the woman gets onto the tester.

In the preferred embodiment, a graphical user interface 72 extends outwardly from the front side 28 of the support frame 22 and is disposed below the head rest 62 and is aligned with the face opening 64 for establishing communication with the prone patient. A computer 74 is electrically connected to the mechanical height adjuster 60 and the graphical user interface 72 and includes a processor 76 and a memory 78 and a plurality of computer programs 80, 82, 84. The plurality of computer programs 80, 82, 84 include a height adjustment program 80 for inputting a plurality of pre-determined heights of the support frame 22 and storing the pre-determined heights in the memory 78 to allow the mechanical height adjuster 60 to automatically select one of the pre-determined heights and elongate the leg 58 according to the selected pre-determined height. In the preferred embodiment, when the mobile diagnostic assembly 20 is to be used with multiple examination surfaces, the height adjustment program 80 will have a preset mode to identify a preset height associated with each of the examination surfaces for allowing an administrator to simply choose one of the examination surfaces. Accordingly, the height of the top 26 will automatically be adjusted to correspond with the height of the chosen examination surface.

The plurality of computer programs 80, 82, 84 also includes a patient information program 82 for displaying a questionnaire on the graphical user interface 72 and receiving a plurality of patient inputs in response to the questionnaire for storage within the memory 78 of the computer 74. This is advantageous because it allows personal data to be easily entered while using the mobile diagnostic assembly 20. In addition, the plurality of computer programs 80, 82, 84 includes a patient entertainment program 84 for storing a plurality of videos in the memory 78 and displaying the videos on the graphical user interface 72 to entertain the prone patient while the diagnostic unit is performing the diagnostic test.

Obviously, many modifications and variations of the present invention are possible in light of the above teachings and may be practiced otherwise than as specifically described while within the scope of the appended claims. That which is prior art in the claims precedes the novelty set forth in the "characterized by" clause. The novelty is meant to be particularly and distinctly recited in the "characterized by" clause whereas the antecedent recitations merely set forth the old and well-known combination in which the invention resides. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims. In addition, the reference numerals in the claims are merely for convenience and are not to be read in any way as limiting.

ELEMENT LIST

| Element Symbol | Element Name |
|---|---|
| A | surface axis |
| P | rolling plane |
| 20 | mobile diagnostic assembly |
| 22 | support frame |
| 24 | bottom |
| 26 | top |
| 28 | front side |
| 30 | rear side |
| 32 | left side |
| 34 | right side |
| 36 | interior |
| 38 | front edge |
| 40 | rear edge |
| 42 | left edge |
| 44 | right edge |
| 46 | caster wheels |
| 48 | opening |
| 50 | flap |
| 52 | chest support |
| 54 | pivot |
| 56 | flap end |
| 58 | legs |
| 60 | mechanical height adjuster |
| 62 | head rest |
| 64 | face opening |
| 66 | face cushion |
| 68 | support hinge |
| 70 | handles |
| 72 | graphical user interface |
| 74 | computer |
| 76 | processor |
| 78 | memory |
| 80 | height adjustment program |
| 82 | patient information program |
| 84 | patient entertainment program |
| $L_f$ | flap length |
| $L_s$ | support length |
| $W_f$ | flap width |
| $W_o$ | opening width |
| $W_s$ | support width |

What is claimed is:

1. A mobile diagnostic assembly (20) including a diagnostic unit and of the type for supporting a patient disposed in a prone position along an examination surface, said assembly (20) comprising:

a support frame (22) having four sides (28, 30, 32, 34) extending between a bottom (24) and a top (26) to define front and rear sides (28, 30, 32, 34) having a support length ($L_s$) being less than or equal to thirty-six inches and left and right sides (32, 34) having a support width ($W_s$) being less than or equal to twenty-four inches and an interior (36) disposed between said top (26) and bottom (24) and inwardly from said sides (28, 30, 32, 34) for housing the diagnostic unit, said top (26) extending between a front and a rear edge (38, 40) to define left and right edges (42, 44), a plurality of caster wheels (46) attached to said bottom (24) and extending to a rolling plane (P) for establishing rolling movement of said assembly (20) over a support to and from a testing position for disposing said rear edge (40) adjacent the examination surface, a plurality of legs (58) extending downwardly from said bottom (24) and disposed in spaced relationship to said rolling plane (P) for rolling movement of said assembly (20), a mechanical height adjuster (60) interconnecting each of said legs (58) with said frame for elongating said legs (58) past the rolling plane (P) to raise said caster wheels (46) from said rolling plane (P) and raise said support frame (22) to align said top (26) with the examination surface, said top (26) defining at least one opening (48) for receiving pendant breasts of the patient in the prone position to allow the diagnostic unit to perform a diagnostic test on the pendant breasts;

said at least one opening (48) including a pair of openings (48) disposed in spaced and aligned relationship relative to a surface axis (A) extending along said top (26) in parallel and equidistant relationship to said left and right edges (42, 44), said top (26) including a chest support (52) extending between said openings (48) and aligned on said surface axis (A), said top (26) being radially deformable relative to said surface axis (A) to establish a concave shape for conforming said top (26) to a shape of the prone patient, said openings (48) defining an opening width ($W_o$) increasing from said surface axis (A) toward said left and right sides (32, 34) for providing access to lymph nodes of the prone patient, a head rest (62) extending from said front edge (38) of said top (26) for supporting a head of the prone patient, said head rest (62) defining a face opening (64) aligned on said surface axis (A) for accommodating a face of the prone patient, a face cushion (66) disposed circumferentially about said face opening (64) and extending upwardly from said head rest (62), a support hinge (68) interconnecting said head rest (62) and said support frame (22) for allowing said head rest (62) to rotate relative to said support hinge (68) and establish parallel and abutting relationship with said front side (28) of said support frame (22), a plurality of handles (70) extending upwardly from said top (26) and disposed next adjacent said left and right edges (42, 44) for assisting the patient in the prone position, a graphical user interface (72) extending outwardly from said front side (28) of said support frame (22) and disposed below said head rest (62) and aligned with said face opening (64) for establishing communication with the prone patient, a computer (74) electrically connected to said mechanical height adjuster (60) and said graphical user interface (72) and including a processor (76) and a memory (78) and a plurality of computer programs (80, 82, 84), said plurality of computer programs (80, 82, 84) including a height adjustment program (80) for inputting a plurality of pre-determined heights of said support frame (22) and storing said pre-determined heights in said memory (78) to allow said mechanical height adjuster (60) to automatically select one of said pre-determined heights and elongate said leg (58) according to said selected pre-determined height, said plurality of computer programs (80, 82, 84) including a patient information program (82) for displaying a questionnaire on said graphical user interface (72) and receiving a plurality of patient inputs in response to said questionnaire for storage within said memory (78) of said computer (74), said plurality of computer programs (80, 82, 84) including a patient entertainment program (84) for storing a plurality of videos in said memory (78) and displaying said videos on said graphical user interface (72) to entertain the prone patient, and characterized by, a flap (50) extending from said rear edge (40) of said top (26) for overlaying the examination surface in said testing position and supporting the prone patient along the examination surface and said flap (50) and said top (26) to prevent movement of said support frame (22) relative to the examination surface, a pivot (54) disposed between said flap (50) and said top (26) for establishing rotation of said flap (50) from said testing position to cover said top (26), said flap (50) extending from said pivot (54) to a flap end (56) to define a flap width ($W_f$) being less than or equal to said support width ($W_s$) for disposing said flap (50) between said left and right edges (42, 44) and a flap length ($L_f$) being less than or equal to said support length ($L_s$) for preventing said flap (50) from extending beyond said front edge (38), and said flap width ($W_f$) being twenty-four inches and said flap length ($L_f$) being twenty-four inches.

\* \* \* \* \*